United States Patent [19]

Tschang et al.

[11] Patent Number: 4,461,832

[45] Date of Patent: Jul. 24, 1984

[54] PREPARATION OF AN ENZYMATICALLY ACTIVE FORMULATION EMBEDDED IN SILICA GEL

[75] Inventors: Chung-Ji Tschang, Frankenthal; Heinrich Klefenz, Hochdorf-Assenheim; Axel Sanner, Frankenthal; Wolfgang Zahn, Altrip, all of Fed. Rep. of Germany

[73] Assignee: BASF Aktiengesellschaft, Fed. Rep. of Germany

[21] Appl. No.: 376,597

[22] Filed: May 10, 1982

Related U.S. Application Data

[63] Continuation of Ser. No. 125,035, Feb. 27, 1980, abandoned.

[30] Foreign Application Priority Data

Mar. 26, 1979 [DE] Fed. Rep. of Germany ....... 2911776

[51] Int. Cl.$^3$ .................... C12N 11/14; B01J 13/02
[52] U.S. Cl. ..................................... 435/176; 264/4.1; 264/4.3; 424/94; 427/213.3; 427/213.32; 435/182; 436/527; 436/535; 436/823; 436/826
[58] Field of Search ................................ 264/4.1, 4.3; 427/213.3, 213.32; 435/176

[56] References Cited

U.S. PATENT DOCUMENTS

| | | | |
|---|---|---|---|
| 2,982,749 | 5/1961 | Friedrich et al. | 526/910 X |
| 3,069,370 | 12/1962 | Jensen et al. | 264/4.1 X |
| 3,791,987 | 2/1974 | Fanger | 264/4 X |
| 3,948,866 | 4/1976 | Pennewiss et al. | 252/9 X |
| 3,954,678 | 5/1976 | Marquisee | 252/62.53 X |
| 4,011,096 | 3/1977 | Sandell | 106/288 B |
| 4,164,613 | 8/1979 | Hoene et al. | 526/201 |

FOREIGN PATENT DOCUMENTS

| | | | |
|---|---|---|---|
| 2625704 | 12/1976 | Fed. Rep. of Germany . | |
| 1267685 | 3/1972 | United Kingdom | 435/176 |

OTHER PUBLICATIONS

Rose et al.: *The Condensed Chemical Dictionary*, 4th Edition, Reinhold Publ. Corp., 1950, p. 710.

*Primary Examiner*—Richard D. Lovering
*Attorney, Agent, or Firm*—Keil & Weinkauf

[57] ABSTRACT

A process for the preparation of an enzymatically active formulation embedded in silica gel, wherein an aqueous mixture of an enzymatically active formulation and a dissolved alkali metal silicate and/or ammonium silicate is suspended in an organic, water-immiscible fluid and then converted to a water-insoluble gel.

11 Claims, No Drawings

PREPARATION OF AN ENZYMATICALLY ACTIVE FORMULATION EMBEDDED IN SILICA GEL

This is a continuation, of application Ser. No. 125,035, filed Feb. 27, 1980 now abandoned.

The present invention relates to a process for the preparation of an enzymatically active formulation embedded in silica gel.

Enzymatically active insoluble formulations are used, inter alia, in medical analysis and in the preparation of base materials for the foodstuff and pharmaceutical industries. They can also be used for the synthesis of optically active substances. The prior art formulations of this type show certain advantages over dissolved or suspended enzymatically active formulations, in respect of ease of separation from the substrate, stability, non-contamination of the reaction products, and the capability of carrying out reactions continuously. However, they are not free from substantial shortcomings. For example, the adsorptive and ionic bonding of the enzymatically active formulation to the carrier in general does not conform to the requirements it has to meet in respect of strength and permanence. Furthermore, the prior art processes require the use of enzymatically active formulations which are in the form of pure, or substantially pre-purified, enzymes. This is true even if the formulation involves a covalent bond, except in cases of crosslinking, which in turn are restricted to cell material and micro-organisms or fragments thereof.

A process which substantially avoids the above disadvantages is disclosed in German Laid-Open Application DOS No. 1,939,347, which describes the preparation of an aqueous silica gel in the presence of an enzymatically active substance. In this process, a jelly-like mass is produced, and it requires expensive measures, entailing large losses, to convert this material into a form suitable for charging into reactors. Furthermore, the starting material for the preparation of the gel is a silica sol which is obtained by a time-consuming and involved process.

We have found a simple process which avoids the above disadvantages.

The present invention relates to a process for the preparation of an enzymatically active formulation embedded in silica gel, wherein an aqueous mixture of an enzymatically active formulation and a dissolved alkali metal silicate and/or ammonium silicate is suspended in an organic, water-immiscible fluid and then converted to a water-insoluble gel.

For the purposes of the invention, enzymatically active formulations are, preferably, particle-bonded enzymes, cell fragments and cell fractions, dried cells, gland secretions, micro-organisms and spores of fungi and micro-organisms. Dissolved, suspended, dispersed or dry enzymes may also be employed.

Specific examples of the above are micro-organisms of the genera Streptomyces, Arthrobacter and Bacillus possessing glucose-isomerase activity, *Escherichia coli* possessing penicillin-acylase activity, Arthrobacter simplex for dehydrogenation of steroids, *Saccharomyces cerevisiae* for reduction of ketones, *Curvularia lunata* for hydroxylation of steroids and *Aspergillus ochraceus* possessing aminoacylase activity. Other suitable materials are trypsin, chymotrypsin, pancreatin, α- and β-amulase, ribonucleases, desoxyribonucleases, cellulase, maltase, pectinase, chitinase, pepsin, bromelain, keratinase, amyloglycosidase, lipase, cholinesterase, lecithinase, phosphatase, alginase, asparaginase, glutaminase, urease, lactase, penicillinamidase, penicillinase, glucose-isomerase, glucose-oxidase, catalase, peroxidase, lipoxidase, xanthin-oxidase, cytochrome-reductase, lactic acid oxidase, aminoacid oxidase, rennin, ficin, subtilisin, tannase, phenol-oxidase, pullulanase, isoamylase, hexokinase, galactose-oxidase, diaphorase, aldolase, glycollic acid oxidase, luciferase, aldehyde-oxidase, naringinase, uricase, glutathione-reductase, nitrito-reductase, nitrate-reductase, succinic acid dehydrogenase, catechol-oxidase, β-fructosidase, aminoacid acylase and urokinase, as well as formulations comprising these enzymes.

Suitable silicate solutions are solutions of sodium silicate, potassium silicate or ammonium silicate of a concentration corresponding to from 8 to 27, preferably from 11 to 24, percent by weight of $SiO_2$.

Preferred water-immiscible solvents are aliphatic, cycloaliphatic and aromatic hydrocarbons and halohydrocarbons, eg. 1,1,1-trichloroethane.

The process of suspension can advantageously be assisted by suspending agents. These include, inter alia, substances used in carrying out water-in-oil suspension polymerizations (inverse suspension polymerizations). Examples are sorbitan esters and the substances referred to in U.S. Pat. No. 2,982,749 and German Laid-Open Application DOS No. 2,009,218, DOS No. 2,634,486 and DOS No. 2,710,372.

The gelling of the silicates is effected in a conventional manner by adding electrolytes or organic water-miscible solvents or, preferably, by lowering the pH by the addition of an agent soluble in water or in the organic fluid.

Gelling is effected particularly efficiently by adding dropwise, to the suspension comprising the organic fluid and the aqueous mixture containing the silicates and the enzymatically active formulation, an organic acid which is soluble in both phases, preferably acetic acid, whereupon neutralization and precipitation occurs. To achieve uniform precipitation, the acid can be diluted with a small amount of the organic fluid. The pH at the end of the precipitation can be adjusted to the appropriate value for the immobilized enzyme formulation by appropriate choice of the amount of acid or acid derivative, for example acid anhydride or acid halide.

Surprisingly, the enzymatic activity remains substantially unaffected by this process, in spite of the exposure to alkali, which lasts for from several seconds to a few minutes, unless a highly alkali-sensitive enzyme is concerned. This exposure to alkali can be minimized by adding a small amount of acid to the alkali metal silicate solution or ammonium silicate solution before mixing it with the enzymatically active substance.

It is advisable, when carrying out the gelling operation, to reduce the swelling of the resulting formulations in water by incorporating inert organic or inorganic materials together with the enzymatically active formulation. This also makes it possible to vary the density of the resulting formulation. Examples of suitable inert materials are pumice powder, glass powder and fibers, kieselguhr, zeolites, organic polymer powders, active charcoal and sparingly soluble salts.

Additional solidification can be achieved by adding soluble sulfates or phosphates to the aqueous silicate mixture and treating the formulation, obtained after gelling, with an aqueous solution of a salt of which the cation forms a sparingly soluble sulfate or phosphate.

Examples of such salts are calcium chloride and barium chloride.

The enzyme formulations prepared by the novel process are very simple to use and are stable over very long periods, even if used frequently.

The Examples which follow illustrate the invention. The micro-organisms mentioned in the Examples merely serve as samples of enzymatically active substances. Should the particular micro-organisms at any time no longer be available, for any reason whatsoever, they can be replaced by any other micro-organisms which possess an enzymatic activity.

EXAMPLE 1

Immobilization of baker's yeast.

Apparatus: 500 ml three-neck flask with stirrer and dropping funnel.

The following mixtures or solutions are prepared:

(1) 0.04 g of a suspending agent (protective colloid A of German Laid-Open Application DOS No. 2,710,372) in 300 ml of toluene, (2) 4.7 g of calcium chloride in 10 ml of water, (3) 7 g of dry baker's yeast and 12 ml of water, (4) 20 g of sodium silicate solution (26% strength, expressed as $SiO_2$), 12 ml of water and 12 ml of 1 N sulfuric acid.

(1) is introduced into the flask. (4) is rapidly mixed with (3) and added to (1), whilst stirring, whereupon the said mixture becomes dispersed as droplets. (2) is added dropwise in the course of 1 minute, whereupon the yeast/silicate mixture solidifies. After stirring for 1 minute, the product is filtered off on a coarse glass frit, washed repeatedly with water and finally dried under reduced pressure at 70° C.

Yield: 13 g of roughly bead-shaped product, particle size <1 mm.

EXAMPLE 2

Immobilization of baker's yeast.

The apparatus and method used were as in Example 1 but, in contrast to the latter, mixture (1) consisted of 0.04 g of suspending agent (protective colloid A of German Laid-Open Application DOS No. 2,634,486), 150 ml of cyclohexane and 150 ml of n-octane and mixture (2) consisted of 4 ml of concentrated hydrochloric acid.

Yield: 7 g of a very finely granular bead-like product.

EXAMPLE 3

Immobilization of baker's yeast.

The apparatus and method used were as in Example 2 but, in contrast to the latter, mixture (2) consisted of 12.1 g of acetic anhydride.

Yield: 14 g of product in bead form.

EXAMPLE 4

Immobilization of baker's yeast.

Apparatus: 1 liter three-neck flask with stirrer and dropping funnel.

The following mixtures or solutions were prepared:

(1) 0.1 g of suspending agent (protective colloid A of German Laid-Open Application DOS No. 2,634,486) in 650 ml of cyclohexane.

(2) 3 g of glacial acetic acid in 25 ml of cyclohexane.

(3) 17.5 g of dry baker's yeast and 35 ml of water.

(4) 50 g of sodium silicate solution (26% strength, expressed as $SiO_2$), diluted with 12.5 ml of water.

The method used was as described in Example 1, but, in contrast to the latter, solution (2) was added dropwise over 5 minutes.

Yield: 23 g of roughly bead-shaped product.

EXAMPLE 5

Immobilization of baker's yeast.

Apparatus: as in Example 4.

The following mixtures or solutions were used:

(1) 0.1 g of suspending agent (protective colloid A of German Laid-Open Application DOS No. 2,634,486), 300 ml of cyclohexane and 300 ml of n-octane.

(2) 5 g of glacial acetic acid in 25 ml of cyclohexane.

(3) 17.5 g of dry baker's yeast, 10 g of pumice powder and 40 ml of water.

(4) 50 g of sodium silicate solution (26% strength, expressed as $SiO_2$), 30 ml of water and 30 ml of 1 N sulfuric acid.

Method:

The precipitation is carried out as in Example 1. After removing the cyclohexane/n-octane mixture under suction, the product is stirred for 30 seconds in 5% strength calcium chloride solution and then completely neutralized by adding 1.25 g of glacial acetic acid, after which stirring is continued for 1 minute. The product is then twice stirred in water for 2 minutes, filtered off and dried at 50° C. under reduced pressure.

Yield: 37.6 g of roughly bead-shaped product.

EXAMPLE 6

Immobilization of baker's yeast.

Apparatus: as in Example 4.

The following mixtures or solutions were used:

(1) 0.1 g of suspending agent (protective colloid A of German Laid-Open Application DOS No. 2,634,486), 325 ml of cyclohexane and 325 ml of n-octane.

(2) 5 g of glacial acetic acid in 25 ml of cyclohexane.

(3) 17.5 g of dry baker's yeast and 30 ml of water.

(4) 50 g of sodium silicate solution (26% strength, expressed as $SiO_2$), 10 ml of water, 20 ml of 4.2% strength aluminum sulfate solution in 1 N sodium hydroxide solution, and 25 ml of 1 N sulfuric acid.

The method was as described in Example 5.

Yield: 31 g of bead-shaped product.

EXAMPLE 7

Immobilization of baker's yeast.

Apparatus: as in Example 4.

The following mixtures or solutions were used:

(1) 0.1 g of suspending agent (protective colloid A of German Laid-Open Application DOS No. 2,634,486) and 300 ml of 1,1,1-trichloroethane.

(2) 60 ml of ethanol.

(3) 31 g of dry baker's yeast and 72 ml of water.

(4) 10 g of sodium silicate solution (26% strength, expressed as $SiO_2$), 5.6 ml of water, 4.4 ml of 4.2% strength aluminum sulfate solution in 1 N sodium hydroxide solution, and 5.6 ml of 1 N sulfuric acid.

(5) 13 ml of 1 N hydrochloric acid, 10 g of calcium chloride and 500 ml of water.

Method:

The precipitation was carried out as in Example 1. After the precipitation, stirring was continued for 5 minutes. Fines were removed by decanting. The precipitated product was then stirred for 4 minutes in (5), washed with water and dried at 50° C. under reduced pressure.

Yield: 20 g of finely granular product.

Yeast content, determined by ignition: 84% by weight.

EXAMPLE 8

Immobilization of *Escherichia coli* (possessing penicillin-acylase activity).

Apparatus: as in Example 4.

The following mixtures or solutions were prepared:

(1) 0.065 g of suspending agent (protective colloid A of German Laid-Open Application No. 2,634,486), 300 ml of cyclohexane and 300 ml of n-octane.

(2) 3,2 g of glacial acetic acid in 15 ml of cyclohexane.

(3) 70 g of an aqueous suspension of *Escherichia coli* ATCC 11,105. Solids content: 15.8% by weight.

(4) 32.1 g of sodium silicate solution (26% strength, expressed as $SiO_2$), 6.5 ml of water, 12.8 ml of 4.2% strength aluminum sulfate solution in 1 N sodium hydroxide solution, and 16 ml of 1 N sulfuric acid.

(5) 350 ml of 5% strength aqueous calcium chloride solution.

Method:

The precipitation was carried out as in Example 1. After having been filtered off, the product was stirred for 1 minute in (5), then washed first with 1% strength and then with 0.5% strength sodium chloride solution, and finally dried at 50° C. under reduced pressure.

Yield: 25 g of bead-shaped product.

EXAMPLE 9

Immobilization of *Streptomyces wedmorensis* (possessing glucose-isomerase activity).

Apparatus: as in Example 4.

The following mixtures or solutions were prepared:

(1) 0.065 g of suspending agent (protective colloid A of German Laid-Open Application DOS No. 2,634,486), 300 ml of cyclohexane and 300 ml of 1,1,1-trichloroethane.

(2) 4 g of glacial acetic acid in 15 ml of cyclohexane.

(3) 75 g of an aqueous suspension of *Streptomyces wedmorensis* ATCC 21,175. Solids content: 15.8% by weight.

(4) 32.1 g of sodium silicate solution (26% strength, expressed as $SiO_2$), 6.5 ml of water, 12.8 ml of 4.2% strength sodium sulfate solution in 1 N sodium hydroxide solution, and 16 ml of 1 N sulfuric acid.

Method:

The precipitation was carried out as in Example 1. After having been filtered off, the product was washed twice, for 2 minutes each time, in 500 ml of 0.5% strength sodium chloride solution and was then dried under reduced pressure at 50° C.

Yield: 20 g of bead-shaped product.

EXAMPLE 10

Immobilization of Arthrobacter species NRRL 3,726 (possessing glucose-isomerase activity).

Apparatus: as in Example 4.

The mixtures used were as in Example 9, except that mixture 3) was 50 g of an aqueous suspension of Arthrobacter species NRRL 3,726, solids content: 25.5% by weight.

The method was as in Example 9.

Yield: 22.7 g of bead-shaped product.

EXAMPLE 11

Immobilization of $\beta$-fructosidase.

Apparatus: as in Example 1.

The following mixtures or solutions were used:

(1) 0.02 g of suspending agent (protective colloid A of German Laid-Open Application DOS No. 2,634,486) in 150 ml of 1,1,1-trichloroethane.

(2) 0.25 g of glacial acetic acid in 5 ml of 1,1,1-trichloroethane.

(3) 50 mg of $\beta$-fructosidase in 5 ml of 0.2 M sodium acetate buffer, pH 4.65.

(4) 10 g of sodium silicate solution (26% strength, expressed as $SiO_2$), 10 ml of water, 4 ml of 4.2% strength aluminum sulfate solution in 1 N sodium hydroxide solution, and 5 ml of 1 N sulfuric acid.

Method:

The precipitation was carried out as in Example 1. After having been filtered off, the product was washed with water and then dried under reduced pressure at room temperature.

Yield: 3.9 g.

EXAMPLE 12

Determination of enzymatic activities.

To determine the invertase activity (for the cases of baker's yeast and $\beta$-fructosidase), 1 g of the formulation was shaken for 1 hour in a 40% strength by weight solution of sucrose in 0.05 M sodium acetate buffer (pH 4.65) at room temperature. The degree of hydrolysis was determined polarimetrically.

To determine the glucose isomerase activity, 1 g of the formulation was shaken for 1 hour, at 70° C., in an aqueous solution of the following substances: 1 M glucose, 0.2 M potassium phosphate buffer, 0.01 M $MgSO_4.7H_2O$ and 0.001 M cobalt chloride.

Thereafter, a sample of the solution, which, depending on the degree of reaction, contained up to 60 mg of fructose, was added to 5 ml of resorcinol reagent (0.05% strength resorcinol in 4 N HCl). The solution was heated for 7 minutes at 80° C. and then cooled for 5 minutes to 5° C. 15 to 30 minutes after cooling, the extinction at 490 nm was measured. The degree of conversion was determined by comparison with a calibration curve.

To determine the penicillin-acylase activity, 1 g of the formulation was shaken in 6 ml of a solution of penicillin G (sodium salt, 35 mg/ml) in 0.05 M potassium phosphate buffer (pH 7.5) at 45° C. After 0, 30 and 60 minutes an 0.1 ml sample was taken and its content of 6-aminopenicillanic acid was determined. The principle of this determination is that a Schiff base is formed from 6-aminopenicillanic acid and p-dimethylaminobenzaldehyde. This base has an absorption maximum at 409 nm. The sample (0.1 ml) containing the 6-aminopenicillanic acid was mixed with 4 ml of 20 percent strength acetic acid and 2 ml of 0.05 M NaOH and the mixture was then centrifuged for 10 minutes in order to exclude any effect of turbidity. 1 ml of a 0.5% strength solution of p-dimethylaminobenzaldehyde in methanol was added to 3.5 ml of the centrifuged solution and thoroughly mixed in. After 15 minutes, the extinction at 409 nm was measured against a sample not containing 6-aminopenicillanic acid. The degree of hydrolysis was deduced from a calibration curve.

The activity yield was determined by comparison with the results achieved under identical conditions, but using non-immobilized enzymatically active substance.

For activity investigations in a column, in contrast to the batch investigations, 0.75 M potassium phosphate buffer (pH 7.5) was used in following the penicillin-acylase activity. The investigation of the glucose-isomerase activity was carried out without a buffer, at pH 8.25, with a magnesium chloride content of 0.004 mole/l.

The content of enzymatically active substance, in the case of immobilization of cell material or micro-organisms, was calculated, based on information gathered from ignition experiments, by using the following empirical formula:

$$G = (T/A) \cdot 100 - 3$$

In this formula, G is the content of enzymatically active substance in the product (in percent by weight), T is the dry weight of enzymatically active substance employed and A is the weight of product obtained according to the Examples (ie. the yield).

The results of the activity determinations are shown in the Table which follows.

agent which is soluble in water and in the organic water-immiscible fluid.

5. A process of claim 4 wherein said agent is an organic acid.

6. A process as set forth in claim 1, wherein the gelling is effected in the presence of an inert material.

7. A process as claimed in claim 1, wherein said enzymatically active formulation embody as micro-organisms one of Streptomyces, Arthrobacter or Bacillus microorganisms, or *Escherichia coli,* Saccharomuces, *Curvularia lunata,* or *Aspergillus ochraceus.*

8. A process as claimed in claim 1, wherein the enzymatically active formulation embody of one of trypsin, chymotrypsin, pancreatin, α- and β-amylase, ribonucleases, desoxyribonucleases, cellulase, maltase, pectinase, chitinase, pepsin, bromelain, keratinase, amyloglycosidase, lipase, cholinesterase, lecithinase, phosphatase, alginase, asparaginase, glutaminase, urease, lactase, penicillin-amidase, penicillinase, glucose-isomerase, glucose-oxidase, catalase, peroxidase, lipoxidase, xanthin-oxidase, cytochrome-reductase, lactic acid oxidase, aminoacid oxidase, rennin, ficin, subtilisin, tannase, phenol-oxidase, pullulanase, isoamylase, hexokinase, galactose-oxidase, diaphorase, aldolase, glycollic acid oxi-

TABLE

| | | | Enzymatic activity of the immobilized substances | | | | |
|---|---|---|---|---|---|---|---|
| | | | Column test | | | Batch test | |
| Formulation from Example No. | Cell content of the formulation (G) % by weight | Substrate | Substrate concentration mg/ml of solution | Flow rate $\left[\dfrac{\text{Column volume}}{h}\right]$ | Conversion % | Residual activity % | Conversion $\left[\dfrac{\text{mg of substrate}}{\text{g of cell formulation} \cdot h}\right]$ |
| 4 | 65 | Sucrose | 400 | 2 | 65 | — | — |
| 5 | 39 | " | 400 | 2 | 70 | 75 | 2,200 |
| 6 | 48 | " | 400 | 2 | 75–80 | 77 | 2,850 |
| 7 | 84 | " | — | — | — | 13.4 | 1,500 |
| 8 | 41 | Penicillin G | 35 | 0.25 | 60 | 8.9 | 342 |
| 9 | 50 | Glucose | 400 | 0.2 | 25 | 83 | 400 |
| 10 | 53 | " | — | — | — | 70 | 360 |
| 11 | — | Sucrose | — | — | — | could not be determined | 250 | dase, luciferase, aldehyde-oxidase, naringinase, uricase, glutathione-reductase, nitrito-reductase, nitrate-reductase, succinic acid dehydrogenase, catechol-oxidase, β-fructosidase, aminoacid acylase and urokinase.

We claim:

1. A process for the preparation of an enzymatically active formulation embedded in silica gel which comprises: suspending an aqueous mixture consisting of an enzymatically active formulation and a dissolved alkali metal silicate and/or ammonium silicate as droplets in a stirred organic, water-immiscible fluid and then converting said silicate to a water-insoluble gel.

2. A process as claimed in claim 1, wherein the enzymatically active formulation used consists of active cells or cell fragments of microbiological, vegetable, animal or human origin.

3. A process set forth in claim 1, wherein the formation of a suspension is assisted by using a suspending agent.

4. A process as set forth in claim 1, 2 or 3, wherein the gelling is effected by lowering the pH by means of an 9. A process as claimed in claim 1, wherein said enzymatically active formulation comprises baker's yeast.

10. A process as claimed in claim 1, wherein the embedded enzymatic formulation is immobilized by the embedding thereof in said gel.

11. A process for the preparation of an enzymatically active formulation embedded in silica gel which comprises: suspending an aqueous mixture consisting of an enzymatically active formulation, soluble sulfates or phosphates and a dissolved alkali metal silicate and/or ammonium silicate as droplets in a stirred organic, water-immiscible fluid, then converting said silicate to a water-insoluble gel, and thereafter treating the product obtained with a solution of salt of which the cation forms a sparingly soluble sulfate or phosphate.

* * * * *